(12) United States Patent
Horiuchi et al.

(10) Patent No.: US 7,944,554 B2
(45) Date of Patent: May 17, 2011

(54) INSPECTION HEAD SUPPORTING STRUCTURE IN SURFACE INSPECTING APPARATUS AND SURFACE INSPECTING APPARATUS

(75) Inventors: Kazuhiro Horiuchi, Kanagawa (JP); Tatsunari Arito, Kanagawa (JP)

(73) Assignee: Kirin Techno-System Company, Limited, Kanagawa (JP)

( * ) Notice: Subject to any disclaimer, the term of this patent is extended or adjusted under 35 U.S.C. 154(b) by 287 days.

(21) Appl. No.: 12/301,275

(22) PCT Filed: May 16, 2007

(86) PCT No.: PCT/JP2007/060040
§ 371 (c)(1),
(2), (4) Date: Dec. 16, 2008

(87) PCT Pub. No.: WO2007/135914
PCT Pub. Date: Nov. 29, 2007

(65) Prior Publication Data
US 2009/0262354 A1    Oct. 22, 2009

(30) Foreign Application Priority Data

May 23, 2006  (JP) ................................. 2006-143034
May 23, 2006  (JP) ................................. 2006-143399

(51) Int. Cl.
*G01N 21/00*    (2006.01)

(52) U.S. Cl. .................................. 356/237.2; 356/237.6
(58) Field of Classification Search .... 356/237.1–237.6, 356/445
See application file for complete search history.

(56) References Cited

FOREIGN PATENT DOCUMENTS

| | | |
|---|---|---|
| JP | 6216460 | 1/1987 |
| JP | 11239902 | 9/1999 |
| JP | 11281582 | 10/1999 |
| JP | 2003050210 | 2/2003 |

*Primary Examiner* — Gregory J Toatley
*Assistant Examiner* — Tri T Ton
(74) *Attorney, Agent, or Firm* — Sughrue Mion, PLLC

(57) ABSTRACT

A pair of angular contact bearings 20A, 20B are disposed between a bearing house 16b of an inspection head 16 and a head supporting tube 8, and a spacer 25 and a spring bearing ring 26 are disposed between outer races 20o of the bearings 20A, 20B. The spacer 25 and the spring bearing ring 26 are urged by a coil spring 27 toward the side of the outer race 20o. An O-ring 28 is disposed between the spacer 25 and the outer race 20o of the bearing 20B, and the outer circumference of the O-ring is brought into closely contact with the inner circumference of the bearing house 16b. The outer races 20o are constrained by a step part 16f in the bearing house 16b and an end cap 29 screwed into the inspection head 16. Removing the end cap 29 makes it possible to take out the bearing housing 16b and a main shaft part 16c integrally from atop of the bearings 20A, 20B.

11 Claims, 8 Drawing Sheets

# US 7,944,554 B2

INSPECTION HEAD SUPPORTING STRUCTURE IN SURFACE INSPECTING APPARATUS AND SURFACE INSPECTING APPARATUS

CROSS-REFERENCE TO PRIOR APPLICATION

This is the U.S. National Phase Application under 35 U.S.C. §371 of International Patent Application No. PCT/JP2007/060040 filed May 16, 2007, which claims the benefit of Japanese Patent Application Nos. 2006-143034 filed May 23, 2006 and 2006-143399 filed May 23, 2006, all of which are incorporated by reference herein. The International Application was published in Japanese on Nov. 29, 2007 as WO2007/135914 A1 under pct article 21(2).

TECHNICAL FIELD

The present invention relates to an inspection head supporting structure in a surface inspecting apparatus, which irradiates an inspection light from an inspection head to an inspection object thereby inspecting the surface of the inspection object, or it relates to a surface inspecting apparatus of inspecting the surface condition of an inspection object.

RELATED ART

As an apparatus of inspecting the inner peripheral surface of a cylindrical inspection object, a surface inspecting apparatus is known which drives out a hollow shaft-like inspection head in the axial direction of the inspection head with rotating the inspection head around its axis, The surface inspecting apparatus inserts the inspection head into the interior of the inspection object, irradiates a laser beam serving as an inspection light from the outer circumference of the inspection head, step scans the inner peripheral surface of the inspection object from one end to the other end along the axial direction, receives the reflection light from the inspection object corresponding to the scan via the inspection head, and determine the condition of the inner peripheral surface of the inspection object, for example the existence of defects or the like on the basis of the light amount of the received reflection light (refer to Patent document 1, for example).

Moreover, as an apparatus of inspecting the surface of an inspection object, for example the inner surface of a cylindrical object, the above surface inspecting apparatus moves a shaft-like inspection head, at the tip of which an optical path changing device is provided, along the axis of the inspection head while rotating the inspection head around the axis by a drive mechanism. Concurrently, the surface inspecting apparatus changes the optical path of the inspection light incident into the interior of the inspection head along the axis by the optical path changing device, and applying the inspection light whose optical path is changed to the inner surface of the hole, and detects the condition of the inner surface on the basis of the light amount of the light reflected from the inner surface and incident again into the interior of the inspection head. In this surface inspecting apparatus, the inspection head is structured in a unit including the optical path changing device. Accordingly, when the optical path changing device is smeared, the entire inspection head is removed from the drive mechanism, and then the optical path changing device is cleaned. Moreover, when the optical path changing device is damaged or when an optical path changing device arranged to fit the inclination of a tapered hole is necessary to inspect the inner surface of the tapered hole, the entire inspection head is replaced.

Patent document 1: JP11-A-281582

SUMMARY OF INVENTION

Problems to be Solved by the Invention

In the above surface inspecting apparatus, it is necessary to speed up the rotation of the inspection head as a provision of enhancing inspection efficiency. However, as the rotation speed of the inspection head is sped up, a higher precision is request for the shake in rotation of the inspection head. In order to fulfill the request, the inspection head supporting structure has to have a reasonable precision. Moreover, when decentering occurs in the inspection head while removing and installing it or replacing it for the purpose of maintenance, and inspection, it becomes necessary to do a work of centering the inspection head. The inspection efficiency might be degraded, when the work takes a time.

Moreover, when the entire inspection head is removed from the drive mechanism and the inspection head is again installed in the drive mechanism, the centering of the inspection head with the drive mechanism has to be done again in addition to the work of removing and installing the inspection head. Then, it takes a relatively long work time. Moreover, when the optical path changing device is replaced, there is also a cost problem for replacing the inspection head.

It is an object of the present invention to provide an inspection head supporting structure able to improve the precision for the shake in rotation of the inspection head and able to reduce or clear the burden of the centering work in removing and installing or in replacing the inspection head. Furthermore, it is another object of the present invention to provide a surface inspecting apparatus able to clean and replace the optical path changing device easily at a low cost.

Means for Solving Problem

An inspection head supporting structure according to an aspect of the present invention, is applied to a surface inspecting apparatus, which irradiates an inspection light to an inspection object from an outer circumference of an inspection head with rotating the inspection head around its axis, receives reflection light reflected from the inspection object to the inspection head, and inspects the surface of the inspection object on the basis of the light amount of the reflection light, wherein the inspection head includes a hollow tubular bearing fitting part and a main shaft part extending to its tip side from the bearing fitting part, the inspection head supporting structure including: a head supporting shaft disposed coaxially inside the bearing fitting part of the inspection head; a pair of bearings, which are disposed with a distance from each other in an axial direction of the inspection head and between an outer circumference of the head supporting shaft and an inner circumference of the bearing fitting part, and which are capable of respectively applying a radial load and a unidirectional axial load; inner race constraining devices, each of which constrains each inner race of the pair of bearings at a constant position in an axial direction on atop of the head supporting shaft; a first and a second pressure preloading members in cylindrical or annular shapes, which are disposed juxtaposed between outer races of the pair of bearings in a movable manner in the axial direction relative to the inspection head; a spring device which is disposed between the first and the second pressure preloading members and each of which urges each pressure preloading member toward each outer race of the pair of bearings; a ring of elastic material disposed between the first pressure preloading member and an outer race of one of the bearings, and an outer circumference of the ring being contacted with the inner circumference of the bearing fitting part; and outer race constraining devices each of which constrains each outer race of the pair of bearings from outside in the axial direction with a first constraining part, which is disposed within the bearing fitting part, and a second constraining part, which is disposed removably and installably at a base end part of the inspection head, wherein, the inspection head is configured to be capable of taken out from atop of the pair of bearings toward the tip side in the axial direction, in a condition wherein the inspection head contains the bearing fitting part and the main shaft part, by removing the second constraining part from the inspection head. Thus, the above problems are solved.

According to the supporting structure of the present invention, when the first and the second pressure preloading members are urged by the spring device, the outer races of the pair of bearings are pushed in outwardly in the axial direction, so that a preload pressure is applied to each of the bearings. In this way, the precision of the shake in rotation of the inspection head can be improved by reducing the looseness in the bearings. When it becomes necessary to remove the inspection head, the inspection head can be integrally removed in a state of containing the bearing fitting part and the main shaft part thereof by removing the second constraining part of the outer race constraining device from the inspection head and taking out the bearing fitting part from atop of the bearings toward the tip side in the axial direction. Then, in installing the inspection head to the bearing, the second constraining part of the outer race constraining device has only to be mounted to the base end part of the inspection head by fitting the bearing fitting part of the inspection head over the outer circumference of the bearing. No separation of the main shaft part from the bearing fitting part is necessary. Since the inspection head can be integrally removed from the bearing in this way without removing the bearing fitting part and the main shaft part, it is not necessary to do a centering work between the bearing fitting part and the main shaft part after installing the bearing fitting part over the bearing. Accordingly, the burden of the centering work in removing and installing or in replacing the inspection head can be reduced or cleared. Furthermore, by bringing the ring of elastic material by the force of the spring device into a close contact with the inner circumference of the bearing fitting part and the outer race of one of the bearing, a friction force can be exerted between these contact surfaces. Thus, even if the acceleration or deceleration in the rotation of the inspection head is increased, a slip is hard to be generated between the bearing fitting part and the outer race of the bearing. Accordingly, by suppressing the wear of the inner surface of the bearing fitting part due to the slip and suppressing the temporal degradation of the precision of the shake in rotation, a high precision of the shake in rotation can be kept over a long period.

In an aspect of the present invention, as the spring device, multiple spring members may be disposed at equal spacing in the circumferential direction of the inspection head and between the pressure preloading members. By urging the pressure preloading member with the multiple spring members in the circumferential direction in a shared manner, preload pressure can be evenly applied to the bearing. Accordingly, the degradation of the rotation performance due to the unbalance of the preload pressure load can be suppressed.

In an aspect of the present invention, an O-ring may be disposed as the ring of elastic material. By using an O-ring, which can be obtained easily as a seal member at a low cost, as ring of elastic material, the supporting structure can be embodied easily at a low cost.

In an aspect of the present invention, a fit tolerance between the outer race of the bearing and the bearing fitting part of the inspection head may be set in a loose fit region. By setting the fit tolerance in the loose fit region, the bearing fitting part can be more easily removed from the bearing. Even the fit tolerance is in the loose fit range, since the ring of elastic material is closely contacted with the bearing fitting part, the looseness in the radial direction might not be generated in the bearing fitting part, and the precision of the shake in rotation is not degraded.

In an aspect of the present invention, the bearing fitting part of the inspection head may be formed in a monolithic structure in which the bearing fitting part is unable to be dismantled from the main shaft part. Since the bearing fitting part and the main shaft part can be integrally removed from the bearing as described above, even when the bearing fitting part and the main shaft part are formed in a monolithic structure, which can not be dismantled, in advance, the inspection head can be removed with no difficulty. Moreover, by forming these in a monolithic structure, the possibility that decentering between the bearing fitting part and the main shaft part might be generated can be eliminated, and the degradation of the precision of the shake in rotation can be prevented in advance.

A surface inspecting apparatus according to another aspect of the present invention, which moves a shaft-like inspection head along its axis with rotating the inspection head around the axis by a drive device, wherein an optical path changing device is provided to a tip of the shaft-like inspection head, and which concurrently changes an optical path of an inspection light incident along the axis into an interior of the inspection head with the optical path changing device, irradiates the inspection light whose optical path is changed to an inspection object, and detects surface condition of the inspection object on the basis of the light amount of the inspection light reflected by the inspection object and incident again into the interior of the inspection head, wherein the inspection head comprises a head main body attached to a drive device, and a holding part which is provided removably and installably to the head main body and which holds the optical path changing device. Thus, the above problem is solved.

According to this surface inspecting apparatus, the inspection head is formed of two members of a head main body attached to the drive device and a holding part which holds an optical path changing device, and the holding part can be removable from and installable into the head main body. Thus, only the holding part can be removed and replaced in replacing the optical path changing device, while keeping the head main body attached to the drive device untouched.

Moreover, in another aspect of the present invention, the holding part may be disposed in a limited manner at the tip side of the inspection head. Since the holding part which is removed and installed is disposed in a limited manner at the tip side of the inspection head in this way, the holding part can be manufactured in a shorter form, and the replacement part can be produced at a low cost.

Furthermore, in another aspect of the present invention, the inspection head may include an inserting part to be inserted into the inspection object, and the holding part may extend toward the side of the drive mechanism farther than the inserting part does.

Thus, a replaceable holding part extends toward the drive device side further than the inserting part does. Thus, when the holding parts having difference lengths are prepared in advance, for example, the holding part can be replaced instantly with a holding part having an appropriated length in accordance with the depth of the inner circumference of a hole to be inspected. Moreover, since a joint part between the head main body and the holder required a removable structure such as a screw, the joint part needs to be thicker than the other parts. However, according to this aspect, since the holder extends to the drive device side further than the inserting part does, the joint position is positioned outside the inserting part. Accordingly, since there exist no joint part in the inserting part, the inserting part can be made in a finer form, and the inspection head with a fine tip can be manufactured so as to able to inspect the interior of a small hole.

Furthermore, the holding part may include an outer tubular body, which is removable from and installable to the head main body, and an inner tubular body, which holds the optical path changing device and is removable from and installable into the interior of the outer tubular body. Since the inner tubular body which holds the optical path changing member can be further removed from the outer tubular body that is removable form the head main body, only the inner tubular body has to be replaced in replacing the optical path changing member, and the replacement can be done at a lower cost Furthermore, in another aspect of the present invention, a tip of the outer tubular body is closed, and a translucent hole is provided to a tubular side surface of the outer tubular body, the both ends of the inner tubular body are opened, a translucent hole is provided to a tubular side surface of the inner tubular body, and a translucent member is fitted into the translucent hole, and slits maybe provided to the inner surface of the tubular side surface so as to be symmetrical with respect to the translucent hole and be inclined at a prescribed angle relative to an axis of the inner tubular body.

In this aspect, a rectangular or circular optical path changing member which is a mirror, for example, can be inserted into the slits of the inner tubular body with its both ends sandwiched between the slits, and the angle of the optical path changing member can be kept easily at a prescribed angle by manufacturing the slits in such a manner that the angle of the slits fits with the inclination of the hole serving as an inspection object. Moreover, since the both ends of the inner tubular body are opened, both spaces inside the inner tubular body divided by the optical path changing member can be easily accessed even after mounting the optical path changing member to the slits of the inner tubular body. Thus, when the inner tubular body as a whole is off balance, the balance can be adjusted easily before installing it to the outer tubular body, for example, by adjusting the position and volume of adhesive agent in the rear space of the optical path changing member. Moreover, when the surface of the optical path changing member is smeared, the smear can be easily wiped out. Furthermore, since the inner tubular body is inserted in to the outer tubular body whose tip is closed, the space where the balance is adjusted by adhesive agent or the like can not be visually observed from outside, and the appearance can not be damaged. Since the inner tubular body and the outer tubular body are provided with translucent holes, the inspection, the optical path thereof is changed by the optical path changing member, can pass through these translucent holes and irradiate the inspection object. However, since a translucent member is fitted into the translucent hole of the inner tubular body, the entry of dust or the like into the interior of the inspection head is prevented.

Effect of Invention

According to the above support structure, the inspection head is rotatably supported by a pair of bearings which are able to burden a radial load and a unidirectional axial load, and moreover, a preload pressure is applied to each of these bearings. Thus, the precision of the shake in rotation of the inspection head can be improved by reducing the looseness of the bearings. Since the inspection head is integrally removable from and installable to the bearings, after installing the bearing fitting part atop of the bearings without removing the bearing fitting part of the inspection head and the main shaft part, it is not necessary to do a centering work between the bearing fitting part and the main shaft part. Accordingly, the burden of the centering work in removing and installing or in replacing the inspection head can be reduced or cleared. Furthermore, the ring of elastic material is brought by the force of the spring device into close contact with the inner circumference of the bearing fitting part and the outer race of one of the bearings, so that a friction force is exerted between these contact surfaces. Thus, even in increasing the acceleration or the deceleration of the rotation of the inspection head, the slip between the bearing fitting part and the outer races of the bearing is hard to be generated. In this way, by suppressing the wear of the inner surface of the bearing fitting part due to the slip and by suppressing the temporal degradation of the precision of the shake in rotation, a high precision of the shake in rotation can be maintained over a long time. Furthermore, by increasing the acceleration and the deceleration of rotation, and thus by reducing the time required for the inspection, inspection efficiency can be improved. Moreover, according to the above surface inspecting apparatus, since the holder of the optical path changing device is removable from and installable to the head main body in the inspection head, only the holder can be removed and replaced in replacing the optical path changing device without removing the head main body attached to the drive device. Thus, the optical path changing device can be cleaned and replaced easily at a low cost.

BEST MODE FOR CARRYING OUT THE INVENTION

Figure 1:
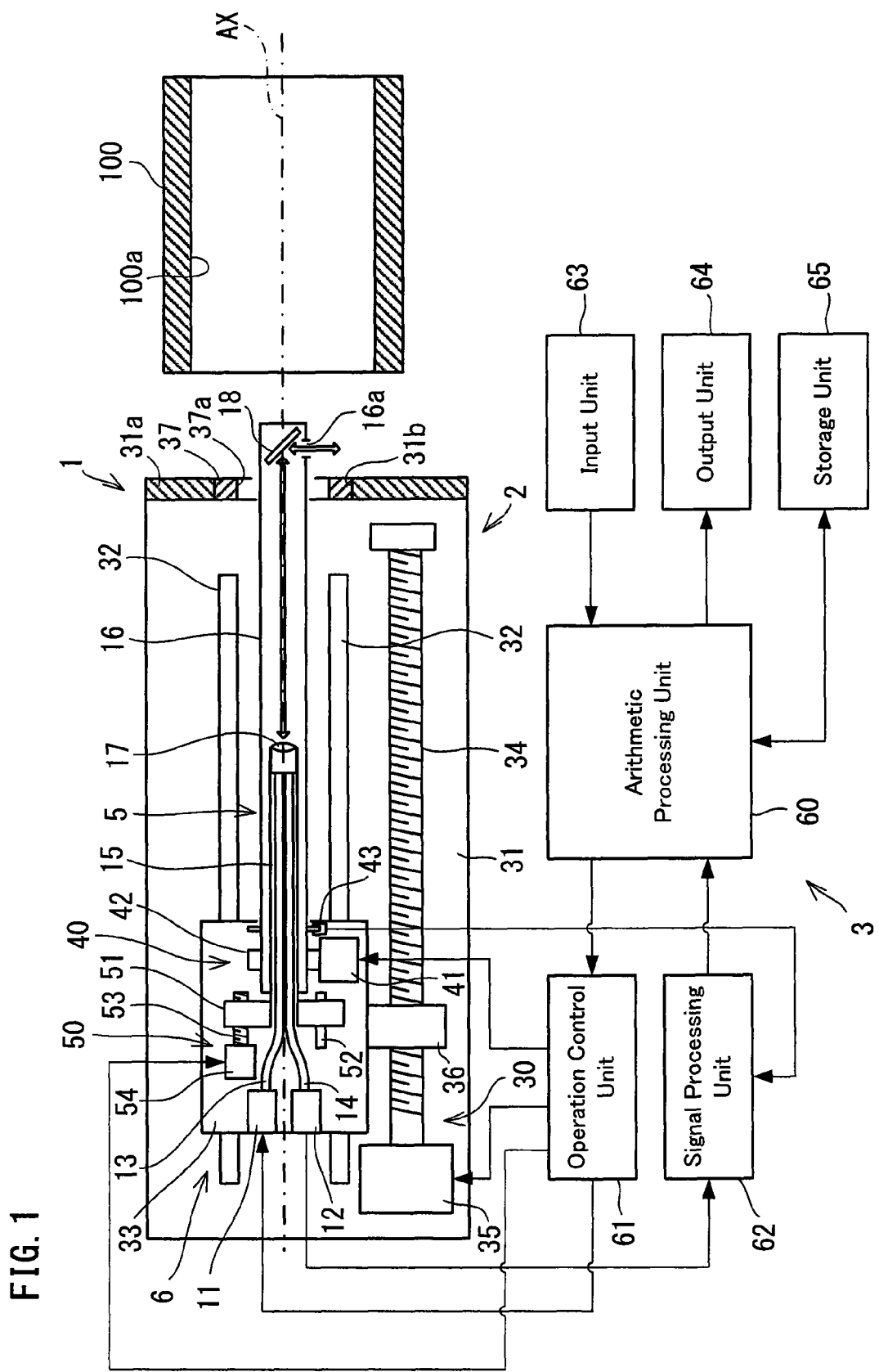
FIG. 1 is a view showing a schematic structure of a surface inspecting apparatus in the first embodiment of the present invention.

FIG. 1 shows a schematic structure of a surface inspecting apparatus in the first embodiment of the present invention. The surface inspecting apparatus 1 is a device suitable for inspecting a cylindrical inner peripheral surface 100a provided to an inspection object 100, and includes an inspection mechanism 2 for executing inspection, and a control unit 3 for executing the operation control of the inspection mechanism 2 and for processing measuring results by the inspection mechanism 2 or the like. Furthermore, the inspection mechanism 2 includes a detection unit 5 serving as the detection device for projecting an inspection light to the inspection object 100 and for receiving a reflection light from the inspection object 100, and a drive unit 6 for making the detection unit 5 to work in a prescribed manner.

The detection unit 5 includes a laser diode 11 (it will be referred as LD in the following) serving as the light source of an inspection light, and a photo detector 12 (it will be referred as PD) which receives the reflection light from the inspection object 100 and outputs a signal of electric current or electric voltage corresponding to the light amount of the reflection light per unit time (the intensity of the reflection light), a light projecting fiber 13 which guide the inspection light projected from the LD 11 toward the inspection object 100, a light receiving fiber 14 for guiding the reflection light from the inspection object 100 to PD 12, a holder tube 15 which holds these fibers 13, 14 in a bundled state, and a hollow shaft-like inspection head 16 disposed coaxially with the holder tube 15 outside thereof. The inspection head 16 is supported rotatably further outside the holder tube 15 via the supporting structure 7 shown in FIG. 2. The details of the supporting structure 7 will be described later.

Returning to FIG. 1, a lens 17 is disposed at the tip of the holder tube 15, which projects the inspection light guided via the light projecting fiber 13 like a beam along the direction of the axis AX of the inspection head 16 (it will be referred as an axial direction in the following) and focuses the reflection light propagating in the reverse direction of the inspection light along the axial direction of the inspection head 16 to the light receiving fiber 14. A mirror 18 serving as an optical path changing device is secured to at the tip part (the right end part in FIG. 1) of the inspection head 1, and a light transmission window 16a is disposed oppositely with the mirror 18 at the outer circumference of the inspection head 16. The mirror 18 changes the optical path of the inspection light projected from the lens 17 toward the light transmission window 16a and changes the optical path of the reflection light incident from the light transmission window 16a into the interior of the inspection head 16 in the direction of propagating toward the lens 17.

The drive unit 6 includes a linear drive mechanism 30, a rotary drive mechanism 40, and a focus adjusting mechanism 50. The linear drive mechanism 30 is provided as a linear drive device for moving the inspection head 16 in the axial direction. In order to realize such a function, the linear drive mechanism 30 includes a base 31, a pair of rails 32 secured on he base 31, a slider 33 movable along the rail 32 in the axial direction of the inspection head 16, a lead screw 34 disposed at the side of the slider 33 in parallel with the axis AX of the inspection head 16, and an electric motor 35 of rotary driving the lead screw 34. The slider 33 functions as a device of supporting the entire detection unit 5. Namely, LD 11 and PD 12 are secured to the slider 33, the inspection head 16 is attached to the slider 33 via the rotary drive mechanism 40, and the holder tube 15 is attached to the slider 33 via the focus adjusting mechanism 50. Furthermore, a nut 36 is secured to the slider 33, and a lead screw 34 is screwed into the nut 36. Accordingly, by rotary driving the lead screw 34 by the electric motor 35, the slider 33 is moved along the rail 32 in the axial direction of the inspection head 16 and this is accompanied by the move of the entire detection unit 5 supported by the slider 33 in the axial direction of the inspection head 16. By the drive of the detection unit 5 using the linear drive mechanism 30, the illumination position (the scanning position) of the inspection light on the inner peripheral surface 100a of the inspection object 100 can be changed in the axial direction of the inspection head 16.

A wall part 31a is disposed at the front end (the right end in FIG. 1) of the base 31, and a through hole 31b coaxially with the inspection head 16 is provided to the wall part 31a. A sample piece 37 is attached to the through hole 31b. The sample piece 37 is provided as a sample for determining the operation condition of the surface inspecting apparatus 1, and a through hole 37a coaxially with the inspection head 16 is provided on its center line. The through hole 37a has an inner diameter at which the inspection head 16 can pass through, and the inspection head 16 goes through the through hole 37a and is driven out into the interior of the inspection object 100.

The rotary drive mechanism 40 is provided as a rotary drive device which rotates the inspection head 16 around the axis AX. In order to realize such a function, the rotary drive mechanism 40 includes an electric motor 41 serving as the rotary drive source and a transmission mechanism 42 of transmitting the rotation of the electric motor 41 to the inspection head 16. A commonly known rotation transmitting mechanism such as a belt transmitting device or a train of gears may be used for a transmission mechanism 42, but a belt transmitting device is used in this embodiment. By transmitting the rotation of the electric motor 41 to the inspection head 16 via the transmission mechanism 42, the inspection head 16 is rotated around the axis AX with accompanying the mirror 18 secured to thereinside. By the rotation of the inspection head 16 using the rotary drive mechanism 40, the illuminate position of the inspection light on the inner peripheral surface 100a of the inspection object 100 can be changed in the circumferential direction of the inspection object 100. Moreover, by combining the move in the axial direction of the inspection head 16 with the rotation thereof around the axis AX, the inner peripheral surface 100a of the inspection object 100 can be scanned by the inspection light over the whole surface thereof. It is noted that the holder tube 15 does not rotate in the rotation of the inspection head 16. Furthermore, the rotary drive mechanism 40 is provided with a rotary encoder 43 which outputs a pulse signal every time the inspection head 16 is rotated by a prescribed unit angle. The number of the pulse signals outputted from the rotary encoder 43 is correlated with the rotation amount (the rotation angle) of the inspection head 16, and the cycle of the pulse signals is correlated with the rotation speed of the inspection head 16.

The focus adjusting mechanism 50 is provided as a focus adjusting device which drives the holder tube 15 in the direction of the axis AX in such a manner that the inspection light focuses on the inner peripheral surface 100a of the inspection object 100. In order to realize such a function, the focus adjusting mechanism 50 includes a supporting plate 51 secured to the base end part of the holder tube 15, a rail 52 disposed between the slider 33 of the linear drive mechanism 30 and the supporting plate 51 and of guiding the supporting plate 51 in the axial direction of the inspection head 16, a lead screw 53 disposed in parallel with the axis AX of the inspection head 16 and screwed into the supporting plate 51, and an electric motor 54 of rotary driving the lead screw 53. By rotary driving the lead screw 53 by the electric motor 54, the supporting plate 51 is moved along the rail 52, and the holder tube 15 is moved in the axial direction of the inspection head 16. In this way, the length of the optical path from the lens 17 to the inner peripheral surface 100a via the mirror 18 can be adjusted in a manner that the inspection light is focused on the inner peripheral surface 100a of the inspection object 100.

Next, the control unit 3 will be described. The control unit 3 includes an arithmetic processing unit 60 serving as the computer unit which performs management of the inspection process by the surface inspecting apparatus 1, processing of measured result of the detection unit 5, and the like; an operation control unit 61 which controls the operation of each unit in the detection unit 5 in accordance with the instructions by the arithmetic processing unit 60; a signal processing unit 62 which executes a prescribed processing on the output signals of PD 12; an input unit 63 for inputting a user's instructions to the arithmetic processing unit 60, an output unit 64 for presenting the inspection result processed by the arithmetic processing unit 60 or the like to the user; and a storage unit 65 of storing a computer program to be executed in the arithmetic processing unit 60, measured data and the like. The arithmetic processing unit 60, the input unit 63, the output unit 64, and the storage unit 65 can be configured by utilizing general purpose computer equipment such as a personal computer. In this case the input unit 63 is provided with input devices such as a keyboard and a mouse, and the output unit 64 is a monitor apparatus. The output device such as a printer may be added to the output unit 64. As the storage unit 65, a storage device such as a hard disk storage device or a semiconductor memory capable of keeping its content can be used. The operation control unit 61 and the signal processing unit 62 may be embodied either by a hardware control circuit(s) or a computer unit(s).

In the case of inspecting the surface of the inner peripheral surface 100a of the inspection object 100, the arithmetic processing unit 60, the operation control unit 61, and the signal processing unit 62 will be operated respectively in the following manner. It is noted that in this case the inspection object 100 is disposed coaxially with the inspection head 16. At the start of the inspection, the arithmetic processing unit 60 instructs the operation control unit 61 to start the necessary operation for inspecting the inner peripheral surface 100a of the inspection object 100 in accordance with the instructions from the input unit 63. The operation control unit 61, which receives the instruction, makes LD 11 to irradiate with a prescribed intensity and concurrently controls the operations of the motors 35 and 41 in such a manner that the inspection head 16 is moved in the axial direction and is rotated around the axis AX at a constant speed. Furthermore, the operation control unit 61 controls the operation of the motor 54 in such a manner that the inspection light focuses on the inner peripheral surface 100a serving as the surface to be inspected. By these controls of the operation, the inner peripheral surface 100a is scanned from one end to the other end thereof by the inspection light. It is noted as for driving out the inspection head 16 in the axial direction that the inspection head 16 may be driven out at a constant speed or moved intermittently with a prescribed pitch for every rotation of the inspection head 16.

Linked with the above scan of the inner peripheral surface 100a, the output signal of PD 12 is guided sequentially to the signal processing unit 62. The signal processing unit 62 executes a necessary analog signal processing in order to process the output signal of PD 12 in the arithmetic processing unit 60, and further AD converts the processed analog signal with a prescribed bit number and outputs the obtained digital signal as a reflection light signal to the arithmetic processing unit 60. Various processing may be used appropriately for the signal processing executed by the arithmetic processing unit 60, including a processing of non-linearly amplifying the output signal so as to enlarge the difference in brightness-darkness of the reflection light detected by PD 12, and a processing of removing noise components from the output signal. Fast Fourier transformation, Inverse Fourier transformation, or the like can be also combined appropriately. Moreover, the A/D conversion by the signal processing unit 62 is executed by utilizing the pulse trains outputted from the rotary encoder 43 as a sampling clock signal. In this way, a digital signal in a tone correlated with the light receiving amount of PD 12 during the period while the inspection head 16 rotates by a prescribed angle is generated and is outputted from the signal processing unit 62.

The arithmetic processing unit 60, which received the reflection light signal from the signal processing unit 62, stores the acquired signal in the storage unit 65. Furthermore, the arithmetic processing unit 60 generates a two-dimensional image of expanding the inner peripheral surface 100a of the inspection object 100 in a planar manner by utilizing the reflection light signal stored in the storage unit 65. The two-dimensional image corresponds to an image of extending the inner peripheral surface 100a in a plain surface defined in the 2D orthogonal coordinate system, in which the circumferential direction of the inspection object 100 is set as the x-direction and the axial direction of the inspection head 16 is set as the y-axial direction, for example. Furthermore, a two-dimensional image in which defect or the like to be detected is emphasized may be generated in generating the two-dimensional image in the arithmetic processing unit 60 by executing an edge processing, a binarize processing, or the like on the original image obtained from the reflection light signal. Then the arithmetic processing unit 60 determines whether the defect or the like exceeding an allowable limit exists on the inner peripheral surface 100a by processing the obtained image with a prescribed algorithm, and outputs the determination result to the output unit 64.

Figure 2:
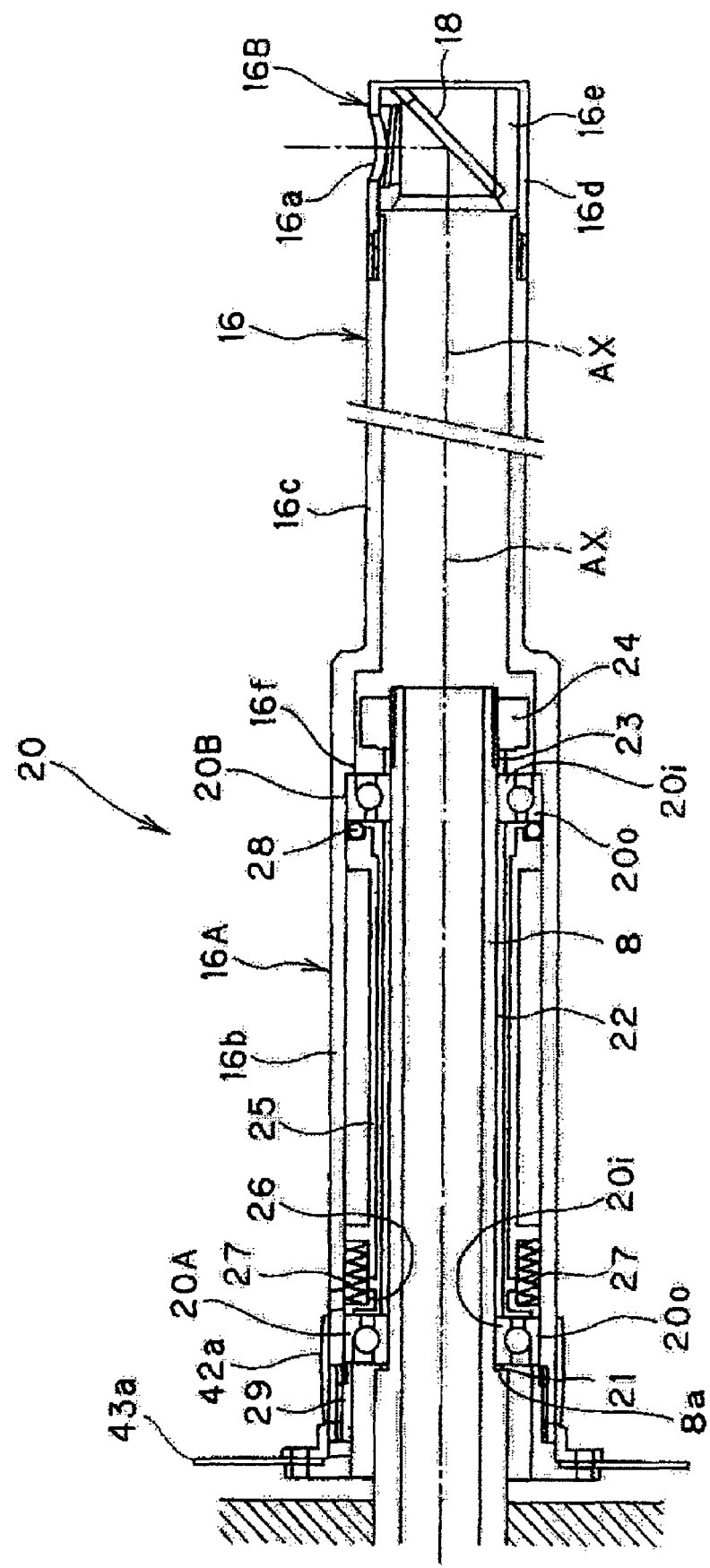
FIG. 2 is a cross sectional view showing an inspection head supporting structure assembled in the surface inspecting apparatus of FIG. 1.

FIG. 2 shows the details of the supporting structure 7 for the inspection head 16. It is noted that in FIG. 2 the right end part of the inspection head 16 corresponds to the tip part of the supporting structure 7 and the left end part corresponds the base end part thereof, respectively. The supporting structure 7 utilizes a head supporting tube 8 disposed between the above holder tube 15 and the inspection head 16 as a head supporting shaft disposed coaxially inside the inspection head 16. The head supporting tube 8 is supported by the slider 33, and the holder tube 15 is inserted in a movable manner inside the head supporting tube 8 along the axial direction. It is noted that the drawing of the holder tube 15 is omitted in FIG. 2. Moreover, the inspection head 16 has a structure of combining a head main body 16A and a mirror housing 16B mounted removably and installably at the tip of the head main body 16A in the axial direction. The head main body 16A is provided with a hollow tubular bearing house 16b serving as the bearing fitting part and a main shaft part 16c extending from the bearing house 16b toward the tip side (the right end side in FIG. 2) of the inspection head 16. The bearing house 16b is also utilized as a part of the supporting structure 7. The bearing house 16b is formed in a monolithic structure in which it can not be dismantled from the main shaft part 16c. For example, the head main body 16A is formed by a cutting work of the bearing house 16b and the main shaft part 16c from a single pipe-like material. The main shaft part 16c is formed to have a smaller diameter than that of the bearing house 16b so as to be inserted into the interior of the inspection object 100. It is noted that the mirror housing 16B includes an outer tube 16d secured coaxially at the tip of the main shaft part 16c and a mirror holding tube 16e secured coaxially to the inner circumference of the outer tube 16d with securing means such as adhesion. The mirror 18 is attached to the mirror holding tube 16e. However, as long as the mirror 18 can be attached at the tip part of the inspection head 16, the mirror housing 16B may be integrated with the head main body 16A as a part of the main shaft part 16c.

A pair of bearings 20A, 20B is disposed between the outer circumference of the head supporting tube 8 and the inner circumference of the bearing house 16b of the inspection head 16 with a distance from each other in the axial direction.

The bearings 20A, 20B are angular contact type ball bearings able to burden a radial load and a unidirectional axial load, respectively. The bearings 20A, 20B are assembled to the outer circumference of the head supporting tube 8 in such a manner that the rear surfaces (the surfaces at the side of the thicker wall) of the respective outer race 20o are opposed to each other. The fit tolerance between the respective outer race 20o of the bearings 20A, 20B and the bearing house 16b is set in a loose fit range in such a manner the inspection head 16 can be easily removed from and installed to the bearings 20A, 20B.

A step part 8a is provided on the outer circumference of the head supporting tube 8, and the inner race 20i of the bearing 20A at the base end side of the inspection head 16 is born against the step part 8a via a washer 21. A sleeve 22 is fitted over the outer circumference of the head supporting tube 8 between the inner races 20i of the bearings 20A, 20B, and a locknut 24 is screwed into the inspection head 16 via a collar 23 at the further tip side from the inner race 20i of the bearing 20B. In this way, the respective inner races 20i of the bearings 20A, 20B are constrained at a constant position on the head supporting tube 8 in the axial direction of the inspection head 16. Namely, the combination of the step part 8a, the washer 21, the sleeve 22, the collar 23, and the locknut 24 function as the inner race constraining device.

A spacer 25 serving as the first pressure preloading member and a spring bearing ring 26 serving as the second pressure preloading member are disposed on the outer circumference of the sleeve 22 with arranged juxtaposed in the axial direction of the inspection head 16. The spacer 25 and the spring bearing ring 26 are rotatable with respect to the sleeve 22 and movable in the axial direction with respect to the bearing house 16b of the inspection head 16. Multiple coil springs 27 are disposed between the spacer 25 and the spring bearing ring 26 at equal spacing in the circumferential direction of the inspection head 16(the rotation direction). Although only two coil springs 27 are shown in FIG. 2, eight coil springs 27 are disposed at equal spacing in the circumferential direction in this embodiment. However, the number of the coil springs 27 may be arbitrary. The coil springs 27 have the same structure. The spacer 25 and the spring bearing ring 26 are urged by these coil springs 27, toward the outer race 20o with circumferentially even force. These coil springs 27 function as the spring device.

An O-ring 28 serving as the ring of elastic material is mounted on the end part of the spacer 25 opposing to the outer race 20o. The O-ring 28 is disposed so as to be respectively contacted with the back surface of the outer race 20o of the bearing 20B and the inner circumference of the bearing house 16b of the inspection head 16. Furthermore, a step part 16f serving as the first constraining part is provided inside the bearing house 16b, and the step part 16f constrains the outer race 20o of the bearing 20B from the tip side in the axial direction of the inspection head 16. An end cap 29 serving as the second constraining part is disposed at the base end side (the left end side in FIG. 2) of the bearing house 16b. The end cap 29 is screwed into the inner circumference of the bearing house 16b. The outer race 20o of the bearing 20A is constrained by the end cap 29 from the base end side in the axial direction of the inspection head 16. Namely, the step part 16f and the end cap 29 function as the outer race constraining device. It is noted that a rotating disk 43a of the rotary encoder 43 is attached to the end cap 29. Moreover, a pulley 42a of the transmission mechanism 42 is attached integrally and rotatably on the outer circumference of the base end side of the bearing house 16b.

The outer race 20o is constrained axially from outside by the step part 16f and the end cap 29, and the coil springs 27 are appropriately compressed in such a state. The spacer 25 and the spring bearing ring 26 are urged toward the outer race 20o by the repulsive force of the coil springs 27 against the compression. In this way, the spring bearing ring 26 is pushed against the back surface of the outer race 20o at the base end side, and preload pressure is applied to the bearing 20A. On the other hand, the O-ring 28 mounted on the spacer 25 is pushed against the back surface of the outer race 20o at the base end side by the force of the coil springs 27, and preload pressure is applied to the bearing 20B. Furthermore, the O-ring 28 is compressed in the axial direction by the force of the coil springs 27, and thus the O-ring 28 is expanded in the radial direction of the inspection head 16. In this way, the O-ring 28 is closely contacted with the inner circumference of the bearing house 16b, and an appropriate friction force is exerted between the both.

According to the above supporting structure 7, angular contact bearings are used as the bearings 20A, 20B for rotatably supporting the inspection head 16, and preload pressure are applied to these bearings 20A, 20B by the force of the coil springs 27. Thus, in comparison with a case of using a general deep groove ball bearing, the looseness in the bearings 20A, 20B can be reduced, and the precision of the shake in rotation of the inspection head 16 can be improved. Moreover, since multiple coil springs 27 are disposed, as the spring device, at equal spacing in the circumferential direction, preload pressure can be applied evenly to the bearings 20A, 20B.

When it becomes necessary to remove the inspection head 16, the inspection head 16 can be taken out from the outer circumferences of the bearings 20A, 20B toward the tip side by rotating the bearing house 16b of the inspection head 16 with respect to the end cap 29 in the direction of loosing the screw. In this way, the head main body 16A of the inspection head 16 or the entire inspection head 16 can be removed at a time. In installing the inspection head 16, the head main body 16A of the inspection head 16 or the entire inspection head 16 can be also installed at a time by inserting the bearing house 16b over the outer circumferences of the bearings 20A, 20B and screwing the end cap 29 into. It is not necessary to do the centering work between the bearing house 16b and the main shaft part 16c thereof after mounting the bearing house 16b. Moreover, the fit tolerance between the outer race 20o of the bearings 20A, 20B and the bearing house 16b is set in the loose fit range, the inspection head 16 can be easily removed from the bearings 20A, 20B. Furthermore, since the spacer 25 is provided with the O-ring 28 and the O-ring 28 is closely contacted with the inner circumference of the bearing house 16b, even in the structure of fitting the bearings 20A, 20B in the bearing house 16b with a loose fit, the looseness in the radial direction might not be generated in the bearing house 16b, and the precision of the shake in rotation is not degraded.

Furthermore, since the O-ring 28 is closely connected to the outer race 20o of the bearing 20B and the bearing house 16b and a friction force is exerted therebetween, even when the acceleration or deceleration in the rotation of the inspection head 16 is improved, the outer race 20o might not slip with respect to the bearing house 16b in the circumferential direction. Accordingly, the wear of the inner surface of the bearing house 16b due to the slip between the outer race 20o and the bearing house 16b might not be generated. Thus, the temporal degradation of the precision of the shake in rotation can also be suppressed, and a high precision of the shake in rotation can be kept over a long period. By increasing the acceleration and deceleration of rotation, it has also an advantage that the inspection efficiency can be enhanced by reducing the time required for the inspection.

The present invention is not limited to the above embodiment, and may be embodied in various forms. For example, in the above embodiment, the spacer 25 and the spring bearing ring 26 may be disposed zigzag in the left-right direction. The first pressure preloading member and the second pressure preloading member are not limited to shapes of a spacer and a spring bearing ring. They may be modified appropriately, as long as they have cylindrical or annular shapes and arranged juxtaposed between the outer races of the bearings in a movable manner in the axial direction. In the above embodiment, an angular contact type ball bearings is used for the bearing, however the bearing is not limited to this type. As long as the bearing has a structure able to burden a radial load and a unidirectional axial load, the precision of the shake in rotation of the inspection head can be improved by applying preload pressure in its axial direction and thus eliminating the looseness in the bearing. As an example, a tapered roller bearing may be used.

The spring device is not limited to a coil spring, and various spring devices such as a disc spring or a leaf spring may be used. The ring of elastic material is not limited to an O-ring, and as long as it has a ring shape and is a member able to deform elastically while the whole circumference thereof is in contact with the inner circumference of the inspection head, it may be changed appropriately.

The monolithic structure of the bearing fitting part and the main shaft part may be varied appropriately, as long as it does not become necessary to do the centering work of the both after installing the inspection head. For example, the both may be integrated by weld-joining the bearing fitting part and the main shaft part, and cutting or grinding at least any one of the bearing fitting part and the main shaft part after the joining so as to align the centers of the both with each other. Even when the bearing fitting part and the main shaft part are jointed with a removable joining device such as a bolt, the bearing fitting part and the main shaft part can be formed as an integrated structure which can not be substantially dismantled, by providing with a decentering preventing device such as a positioning pin after centering of the both thereby removing the possibility of decentering between the both. Furthermore, even when the bearing fitting part and the main shaft part are formed in a structure which can be dismantled, as long as the bearing fitting part can be taken out from the bearing toward the tip side in the axial direction of the inspection head without dismantling the bearing fitting part and the main shaft part, it is also unnecessary to dismantle the inspection head the bearing fitting part and the main shaft part in installing the inspection head, and thus the burden of centering work can be reduced or cleared.

The inspection head supporting structure of the present invention can be applied to the surface inspecting apparatus in various forms, as long as the inspection head is rotated around its axis. For example, the supporting structure of the present invention can be applied even to the surface inspecting apparatus having no mechanism of moving the inspection head in the axial direction. The shape of the inspection head or the structure for irradiating an inspection light and receiving the reflection light is also not limited to the above embodiment, and appropriate modifications are possible. For example, the supporting structure of the present invention can be applied even to the surface inspecting apparatus in which an emitting element(s) and a receiving element(s) are provided on the outer circumference of the inspection head.

Figure 3:
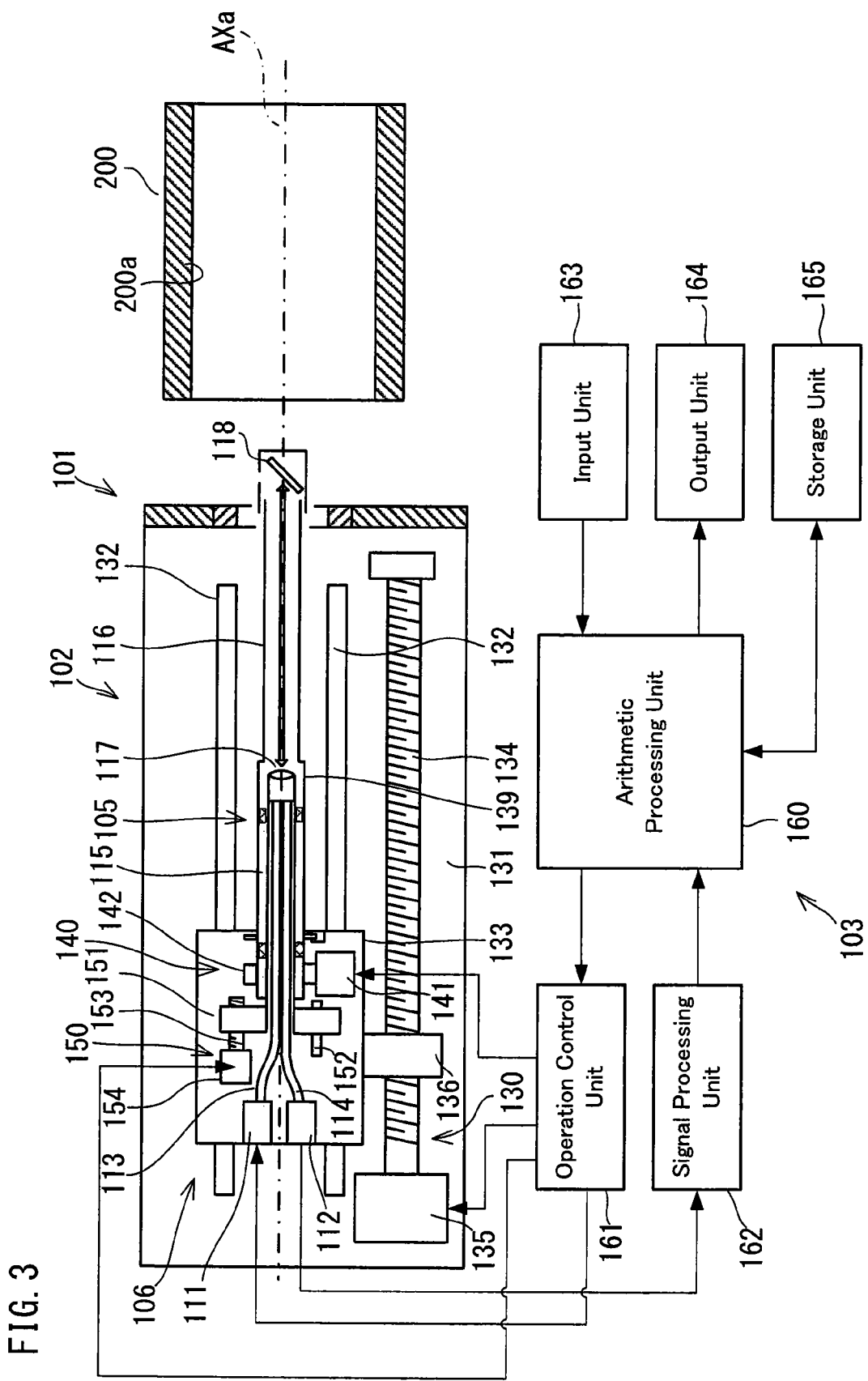
FIG. 3 is a view showing a schematic structure of a surface inspecting apparatus in the second embodiment of the present invention.

FIG. 3 shows a schematic structure of a surface inspecting apparatus in the second embodiment of the present invention.

The surface inspecting apparatus 101 is a device suitable for inspecting a cylindrical inner peripheral surface 200a provided to an inspection object 200, and includes an inspection mechanism 102 for performing inspection, and a control unit 103 for executing the control operation of the inspection mechanism 102 and the processing of the measuring results by the inspection mechanism 102 or the like. Furthermore, the inspection mechanism 102 includes a detection unit 105 which projects an inspection light to the inspection object 200 and receives the reflection light from the inspection object 200, and a drive unit 106 which makes the detection unit 105 to work in a prescribed manner.

The detection unit 105 includes a laser diode (LD) 111 serving as the light source of the inspection light, a photo detector 112 (it will be referred as PD in the following) which receives the reflection light from the inspection object 200 and outputs the electric signal of electric current or electric voltage corresponding to the light amount of the reflection light per unit time (intensity of the reflection light), a light projecting fiber 113 which guides the inspection light irradiated from LD 111 toward the inspection object 200, a light receiving fiber 114 for guiding the reflection light from the inspection object 200 to PD 112, a holder tube 115 which holds these fibers 113, 114 in a bundled form, and a hollow shaft-like inspection head 116 disposed coaxially outside the holder tube 115. It is noted that the details of the inspection head 116 will be described later. A lens 117 is disposed at the tip of the holder tube 115, and the lens projects the inspection light, which has guided via the light projecting fiber 113, in a shape of a beam along the direction of the axis AXa of the inspection head 116 (it will be referred as the direction of the axis AXa in the following) and focuses the reflection light, which propagates in the opposite direction of the inspection light along the direction of the axis AXa of the inspection head 116, on the light receiving fiber 114. A mirror 118 serving as an optical path changing device is disposed at the tip (the right end part in FIG. 3) of the inspection head 116.

The drive unit 106 includes a linear drive mechanism 130, a rotary drive mechanism 140, and a focus adjusting mechanism 150. The linear drive mechanism 130 is provided as a linear drive device for moving the inspection head 116 in the direction of their axis AXa. In order to realize such a function, the linear drive mechanism 130 includes a base 131, a pair of rails 132 secured to the base 131, a slider 133 movable along the rail 132 in the direction of the axis AXa of the inspection head 116, a lead screw 134 disposed at the side of the slider 133 in parallel with the axis AXa of the inspection head 116, and an electric motor 135 of rotary driving the lead screw 134. The slider 133 functions as a device of supporting the entire detection unit 105. Namely, LD 111 and PD 112 are secured to the slider 133, and the inspection head 116 is attached to the slider 133 via the rotary drive mechanism 140. The holder tube 115 is attached to the slider 133 via the focus adjusting mechanism 150. Furthermore, the lead screw 134 is screwed into a nut 136 that is secured to the slider 133. Therefore, by rotary driving the lead screw 134 by the electric motor 135, the slider 133 is moved along the rail 132 in the direction of the axis AXa of the inspection head 116, the entire detection unit 105 supported by the slider 133 is moved together with the move in the direction of the axis AXa of the inspection head 116. By driving the detection unit 105 by using the linear drive mechanism 130, the illumination position of the inspection light on the inner peripheral surface 200a of the inspection object 200 can be varied in the direction of the axis AXa of the inspection head 116.

The rotary drive mechanism 140 is provided as a rotary drive device of rotating the inspection head 116 around the axis AXa. In order to realize such a function, the rotary drive mechanism 140 includes bearings 139 which are installed between the holder tube 115 and the inspection head 116 so as to supports the inspection head 116 in a rotatable manner around the axis AXa, an electric motor 141 serving as the rotary drive source, and a belt 142 serving as the transmission mechanism of transmitting the rotation of the electric motor 141 to the inspection head 116. It is noted that a transmission mechanism is not limited to the belt 142, and other rotation transmitting mechanism such as a gear train can be utilized. The inspection head 116 together with the mirror 118 is rotated around the axis AXa by transmitting the rotation of the electric motor 141 to the inspection head 116 via the belt 142. Through the rotation of the inspection head 116 by using the rotary drive mechanism 140, the illumination position of the inspection light on the inner peripheral surface 200a of the inspection object 200 can be varied in the circumferential direction of the inspection object 200. Then, by combining the move in the axial direction of the inspection head 116 and the rotation around the axis AXa, it becomes possible to scan the whole inner peripheral surface 200a of the inspection object with an inspection light.

The focus adjusting mechanism 150 is provided as a focus adjusting device which drives the holder tube 115 in the direction of the axis AXa in such a manner that the inspection light focuses on the inner peripheral surface 200a of the inspection object 200. In order to realize such a function, the focus adjusting mechanism 150 includes a supporting plate 151 secured to the base end part of the holder tube 115, a rail 152 disposed between the slider 133 of the linear drive mechanism 130 and the supporting plate 151 and of guiding the supporting plate 151 in the axial direction of the inspection head 116, a lead screw 153 disposed in parallel with the axis AXa of the inspection head 116 and screwed into the supporting plate 151, and an electric motor 154 of rotary driving the lead screw 153. By rotary driving the lead screw 153 by the electric motor 154, the supporting plate 151 moves along the rail 152, and the holder tube 115 moves in the direction of the axis AXa of the inspection head 116. Accordingly, the length of the optical path from the lens 117 to the inner peripheral surface 200a via the mirror 118 can be adjusted in a manner that the inspection light is focused on the inner peripheral surface 200a of the inspection object 200.

The control unit 103 includes an arithmetic processing unit 160 serving as the computer unit which performs management of the inspection process by the surface inspecting apparatus 101, processing of measured result, and the like; an operation control unit 161 which controls the operation of each unit in the inspection mechanism 102 in accordance with the instructions by the arithmetic processing unit 160; a signal processing unit 162 which executes a prescribed processing on the output signals of PD 112; an input unit 163 for inputting a user's instructions to the arithmetic processing unit 160, an output unit 164 for presenting the measurement result in the arithmetic processing unit 160 or the like to the user; and a storage unit 165 of storing a computer program to be executed in the arithmetic processing unit 160, measured data and the like. The arithmetic processing unit 160, the input unit 163, the output unit 164, and the storage unit 165 can be configured by utilizing general purpose computer equipment such as a personal computer. In this case the input unit 163 is provided with input devices such as a keyboard and a mouse, and the output unit 164 is a monitor apparatus. The output device such as a printer may be added to the output unit 164. As the storage unit 165, a storage device such as a hard disk storage device or a semiconductor memory capable of keeping its content can be used. The operation control unit 161 and the signal processing unit 162 may be embodied either by a hardware control circuit(s) or a computer unit(s).

Figure 4:
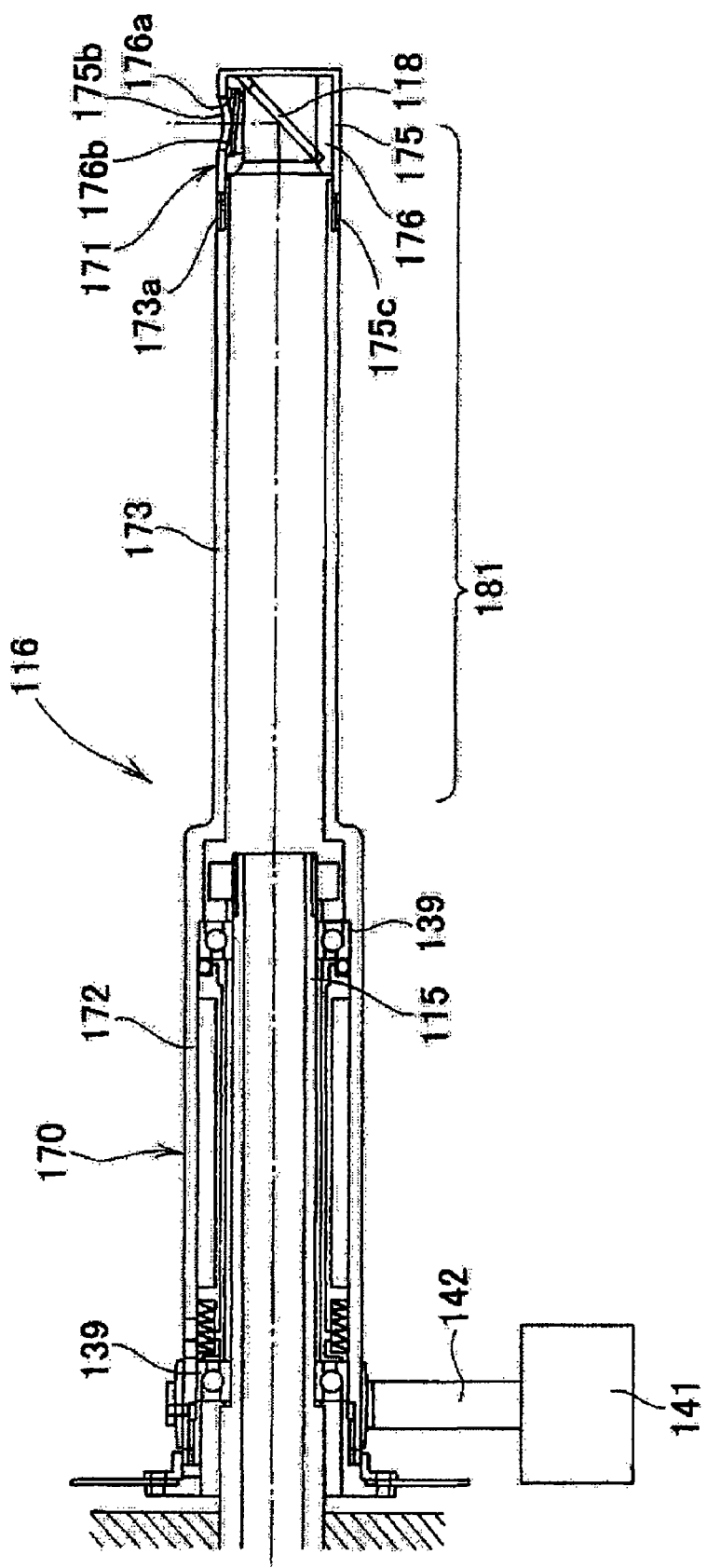
FIG. 4 is an enlarged view of the inspection head shown in FIG. 3.

FIG. 4 is an enlarged view of the inspection head 116. As described above, the inspection head 116 includes a head main body 170 attached to the electric motor 141 via the belt 142, and a holding part 171 disposed removably and installably at the tip of the head main body 170 and holding the mirror 118.

The head main body 170 includes a holder tube exterior part 172 mounted rotatably around the holder tube 115 via the bearings 139 and a hollow extension part 73 extending toward the tip thereof from the holder tube exterior part 172 in the axial direction. The tip of the hollow extension part 173 is cut away in such a manner that the outer diameter thereof gets smaller, and a threaded part 173a is provided to the cut-away part.

Figure 5A:
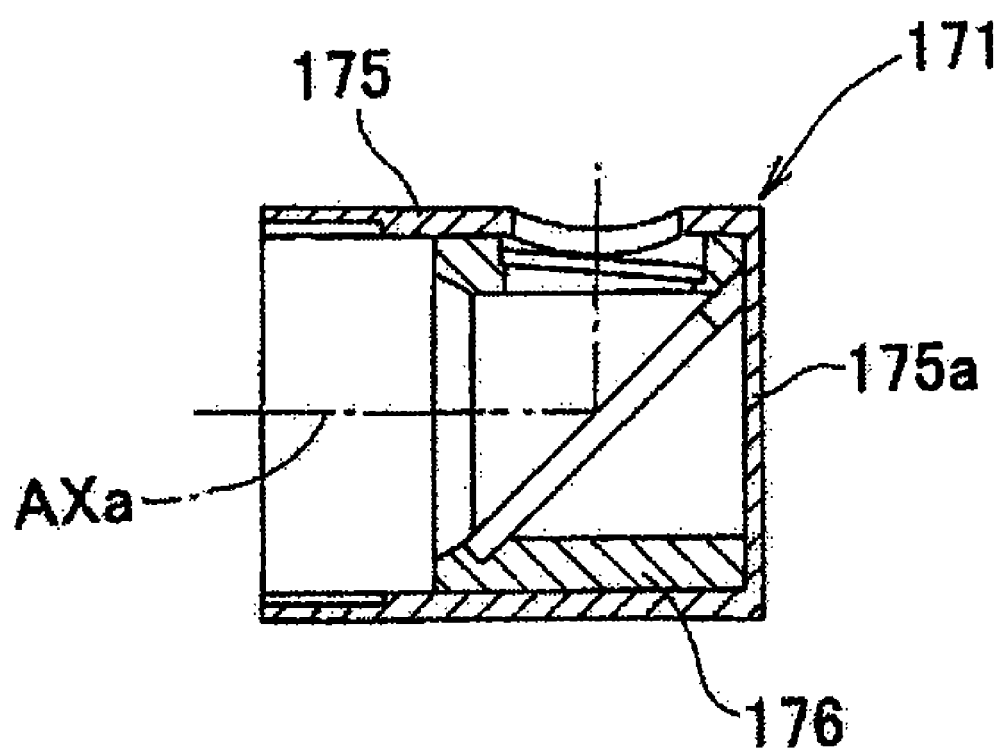
FIG. 5A is a cross sectional view of the entire holder.

The holding part 171 includes an outer tubular body 175 which is removable from and installable to the hollow extension part 173 of the head main body 170, and an inner tubular body 176 which holds the mirror 118 and is removable from and installable into the interior of the outer tubular body 175. FIG. 5A is a cross sectional view of the entire holding part 171, FIG. 5B is a cross sectional view of the outer tubular body 175, and FIG. 5C is a cross sectional view of the inner tubular body 176.

Figure 5B:
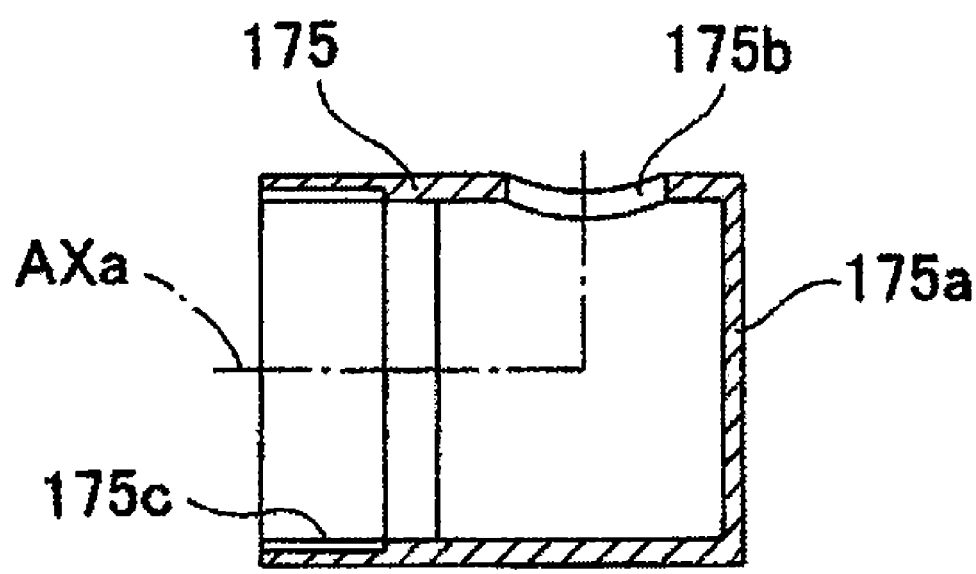
FIG. 5B is a cross sectional view of the outer tubular body.

The outer tubular body 175 shown in FIG. 5B is a tubular body of which the tip 175a is closed, and a circular translucent hole 175b is provided to the tubular side surface of the tubular body. Moreover, a threaded part 175c is provided inside the other end of the outer tubular body 175.

Figure 5C:
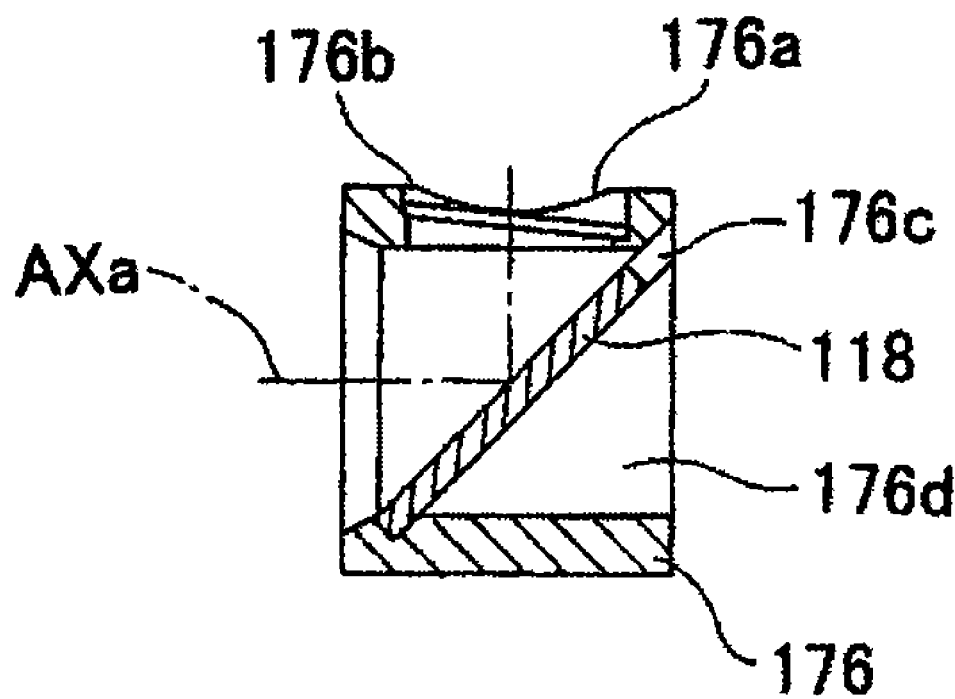
FIG. 5C is a cross sectional view of the inner tubular body.

In the inner tubular body 176 shown in FIG. 5C, the both ends thereof are opened and a circular translucent hole 176a having a larger diameter than that of the translucent hole 175b of the outer tubular body 175 is provided to the tubular side surface thereof. A translucent member 176b such as glass, for example, is fitted into the translucent hole 176a. Moreover, slits 176c are provided to both sides of the inner surface of the inner tubular body 176 which are symmetrical with respect to the translucent hole 176a, and the slits are is inclined at a prescribed angle with respect to the axis AXa, and a mirror 118 is fitted into the slit 176c.

The operation of this embodiment will be described in the following. First, the surface inspecting apparatus 101 is disposed in such a manner that the axis of the inspection object 200 is aligned with the axis AXa as shown in FIG. 3. An inner tubular body 176 is prepared, in which slits 176c are provided to able to dispose a mirror 118. The mirror 118 is disposed at an angle at which the optical path of the inspection light propagating along the axis AXa is changed such that the inner peripheral surface 200a of the inspection object 200 inclined at a prescribed angle with respect to the axis AXa (the inner peripheral surface 200a is in a parallel state inclined at an angle of 0° with respect to the axis AXa in FIG. 3) is perpendicularly illuminated by the inspection light. Then, the mirror 118 is disposed to the slits 176c as shown in FIG. 5C. When the gravity center of the inner tubular body 176 is not on the axis AXa in the state where the mirror 118 is disposed, the balance of the entire inner tubular body 176 is adjusted by adjusting the position and volume of adhesive agent for fixing the mirror 118 in the rear space 176d of the mirror 118. Thus, according to this embodiment, since the both ends of the inner tubular body 176 are opened and thus the rear space 176d of the inner tubular body 176 is accessible, the balance of the inner tubular body 176 can be easily adjusted.

Next, the inner tubular body 176 is inserted into the interior of the outer tubular body 175 from the front surface of the outer tubular body 175, and is arranged such that the center of the translucent hole 175b of the outer tubular body 175 is aligned with the center of the translucent hole 176a of the inner tubular body 176, and thereby completing the holding part 171. According to this embodiment, since the tip 175a of the outer tubular body 175 is closed, the rear space 176d of the mirror 118, where the balance is adjusted by the adhesive agent or the like, is not visually observed from outside, and the appearance can not be damaged.

Then, the holding part 171 is secured at the end part of the head main body 170 as shown in FIG. 4 by screwing the threaded part 175c of the outer tubular body 175 into the threaded part 173a at the end part of the head main body 170, and thereby completing the inspection head 116. In this case, it can be mounted easily, since it is a screw mount type. It is noted that the holding part 171 and the hollow extension part 173 of the head main body 170 serve as the inserting part 181 to be inserted inside the inner surface 200a of the inspection object 200.

Next, the holder tube exterior part 172 of the head main body 170 is mounted outside the holder tube 115 via the bearings 139, and the centering of the head main body 170 with the holder tube 115 is performed by a centering mechanism (not shown). Thereafter, when the start of the operation is instructed from the input unit 163 shown in FIG. 3, the start of the necessary operation for inspecting the inner peripheral surface 200a of the inspection object 200 is instructed from the arithmetic processing unit 160 to the operation control unit 161. The operation control unit 161 which receives the instruction makes LD 111 to irradiate at a prescribed intensity and concurrently controls the operations of the motors 135 and 141 in such a manner that the inspection head 116 moves at a constant speed in the direction of the axis AXa and rotates around the axis AXa at a constant speed. Furthermore, the operation control unit 161 controls the operation of the motor 154 in such a manner that the inspection light focuses on the inner peripheral surface 200a serving as a surface to be inspected. By those operation controls, the inspection light goes from LD 111 through the light projecting fiber 113 via the lens 117, thereafter, propagates in the hollow extension part 173 along the axis AXa, the optical path is changed by the mirror 118 of the holder 17, goes through the translucent hole 176a and the translucent hole 175b by passing through the translucent member 176b, and scans the inner peripheral surface 200a helically from one end to the other end. It is noted in the inspection of the inner surface 200a that dust or the like does not enter into the interior of the holding part 171 during inspection since the translucent member 176b is fitted into the translucent hole 176a of the inner tubular body 176.

Then, among the inspection light applied on the inner peripheral surface 200a, the light which is reflected by the inner peripheral surface 200a and reaches the translucent hole 175b passes through the translucent hole 176a by going through the translucent member 176b, and the optical path thereof is again changed at the mirror 118 to, propagated oppositely in the hollow extension part 173 along the axis AX, and goes through the lens 117, incidents on the light receiving fiber 114, and is guided to PD 112 shown in FIG. 3. Then, the light guided to PD 112 is sent to the signal processing unit 162, the reflection light signal outputted from the signal processing unit 162 is processed by the arithmetic processing unit 160, and is displayed by the output unit 164 as a two-dimensional image. Then, the condition of the inner surface is grasped by the two-dimensional image.

When the mirror is smeared or when the mirror is broken in the process of inspecting in this manner or when it is necessary to inspect the inner peripheral surface 200a having a different inclination, it becomes necessary to clean or replace the mirror. In this case, by rotating the holding part 171 with respect to the head main body 170, the threaded part 175c of the holding part 171 is taken out from the threaded part 173a of the head main body 170. Then, the inner tubular body 176 is pulled out of the outer tubular body 175. Thereafter, when the mirror is smeared, cleaning such as wiping out smear of the mirror is performed. In this case, since the both ends of the inner tubular body 176 are opened, the surface of the mirror can be cleaned easily. When the mirror is broken, the mirror is replaced, or it is replaced with another inner tubular body 176 to which a new mirror is attached with the inner tubular body 176. When inspecting a hole with a different inclination it is replaced with the inner tubular body 176 to which a mirror 118 is mounted in the slits 176c provided at a different angle. In this case also, when the gravity center of the inner tubular body 176 is not located on the axis AXa, it becomes necessary to adjust the balance adjustment before inserting the inner tubular body 176 into the interior of the outer tubular body 175. However, since the front end of the inner tubular body 176 is opened the rear surface space 176b of the mirror 118 can be easily accessed, and the balance of the mirror 118 can be easily adjusted.

Next, in similar manner to the above, the inner tubular body 176 is inserted into the interior of the outer tubular body 175 from the front surface of the outer tubular body 175 does, and is arranged in such a manner that the center of the translucent hole 175b of the outer tubular body 175 is aligned with the center of the translucent hole 176a of the inner tubular body 176, so as to complete the holding part 171. In this case also, since the front surface of the outer tubular body 175 is closed, the back surface space of the mirror 18, where the balance is adjusted with adhesive agent or the like is visually not observed from outside, and the appearance is not damaged.

Then, the holding part 171 is secured to the head main body 170 by screwing the threaded part 175c of the outer tubular body 175 into the threaded part 173a provided to the tip of the head main body 170, thereby completing the inspection head 116 again. In this case, the head main body 170 has been already centered with the rotary drive mechanism 130, readjustment is not necessary.

As described above, according to this embodiment, since the holding part 171 of the mirror 118 is removable from and installable to the head main body 170 in the inspection head 116, only the holding part 171 can be removed and replaced, in a case of replacing the mirror 118, without removing the head main body 170 attached to the rotary drive mechanism 140. Thus, the mirror 118 can be cleaned and replaced easily at a low cost.

Figure 6:
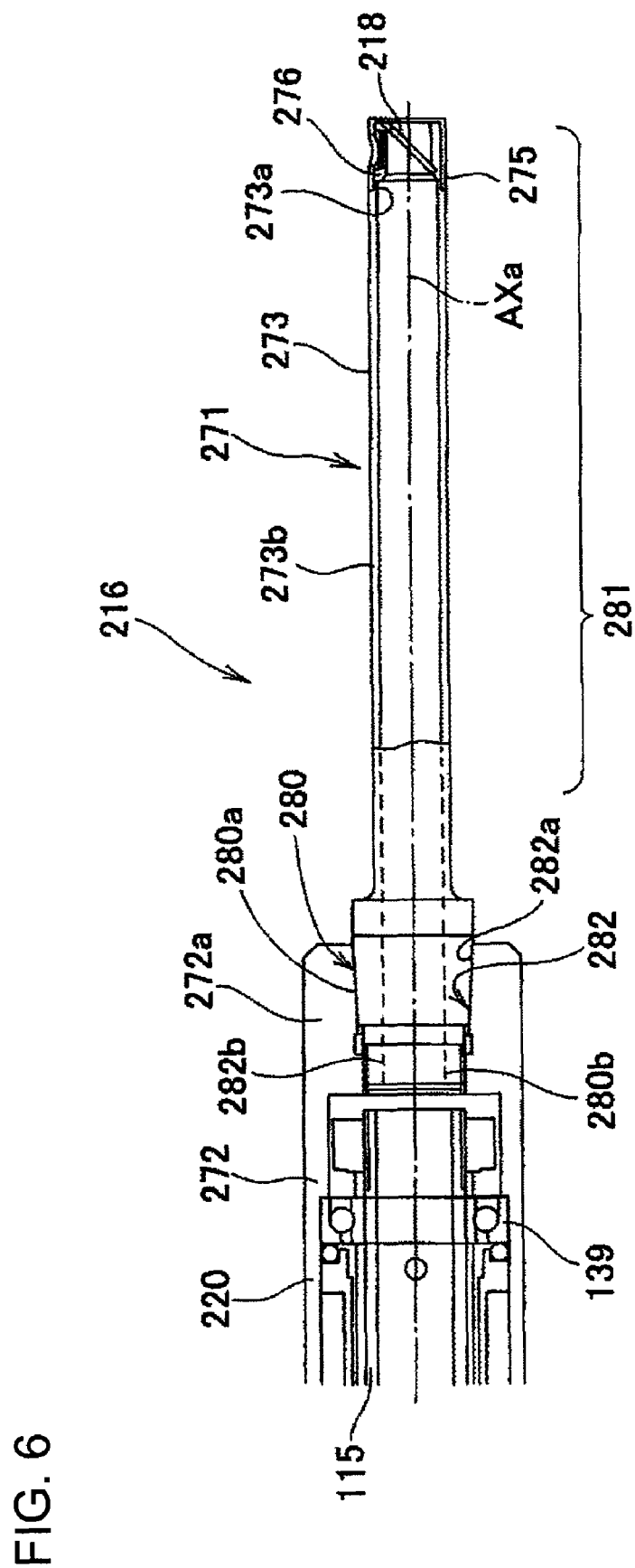
FIG. 6 is a view showing an inspection head of the surface inspecting apparatus in the third embodiment of the present invention.

Next, the third embodiment of the surface inspecting apparatus of the present invention will be described. FIG. 6 is a view showing an inspection head 216 of the surface inspecting apparatus of the present invention in the third embodiment. It is noted that since this embodiment and the second embodiment are same except for the inspection head 216 descriptions of the parts other than the inspection head 216 will be omitted.

The inspection head 216 includes a rotary drive mechanism, a head main body 220 attached to a linear drive mechanism via the rotary drive mechanism, and a holding part 271 removably and installably attached to the head main body 220 and holding a mirror 218, which is an optical path changing member in a similar manner to the inspection head 216 in the second embodiment. Hoverer, it differs from the second embodiment in that the head main body 220 does not include the inserting part 281 to be inserted into the inspection object, namely, in that the hollow extension part 273 extending in the center of the inspection head is not included by the head main body 220 but is included in the holding part 271.

The holding part 271 includes an outer tubular body 275 and an inner tubular body 276 which are disposed at the tip thereof, a hollow extension part 273 extending from the outer tubular body 275 along the axis AXa to the drive mechanism side, and an inserting part 280 disposed at the base end part of the hollow extension part 273. The inner tubular body 276 has the same shape as the inner tubular body 176 in the second embodiment. The outer tubular body 275 has also the substantially same shape as the outer tubular body 175 in the second embodiment, but it differs therefrom in that no threaded part is provided to the inner side surface at the opening side. Moreover, no threaded part is provided to the tip of the hollow extension part 273, but a cut-away part 273*a* is provided which is cut away in such a manner the outer diameter thereof gets smaller. The outer diameter of the cut-away part 273*a* is almost equal to the inner diameter of the outer tubular body 275. The outer diameter of the middle part 273*b* of the hollow extension part 273 extending from the cut-away part 273 to the drive mechanism side is equal to the outer diameter of the outer tubular body 275. Then, the outer tubular body 275 is fitted into and adheres to the tip of the hollow extension part 273 in the condition that the inner tubular body 276 is disposed thereinside, the inserting part 281 having an even diameter as a whole is formed. The outer diameter at the base end part of the hollow extension part 273 gets enlarged. A tapered part 280*a* is provided which gets gradually smaller in the diameter from here in the direction toward the drive mechanism side, and a threaded part 280*b* is provided at the further ahead thereof, and thus an inserting part 280 is formed.

The head main body 220 is a tubular member including a holder tube exterior part 272 mounted outside the holder tube 115 via the bearings 139. The thick wall of the tip thereof is formed along the axis, a taper part 282*a* is provided on the inner circumference of the cylindrical member in the thick wall part 272*a*, the taper part 282*a* gets gradually smaller in the diameter in the direction from the tip toward the drive mechanism side, a threaded part 282*b* is provided at the further ahead thereof, and thus the receiving part 282 for receiving the above inserting part 280 is formed.

In this embodiment, the outer tubular body 275 and the hollow extension part 273 are formed not with a removable structure such as internal threading but by simply fitting one of the two cylindrical members into the other and bonding them with an adhesive agent or the like. Thus, they can be manufactured in a thinner form than a case in which they have a removable structure provided with a threaded part or the like at that part. Thus, the diameter of the inserting part 281 can be made smaller, and the inner peripheral surface of a small hall can also be inspected. Moreover, the holding part 271 removable from and installable to the head main body 220 extends further to the drive mechanism side than the inserting part 281 to be inserted into the inspection object. Therefore, once the holding parts 271 having different lengths are prepared in advance, for example, the holding part 271 can be replaced with the one having an appropriate length in accordance with the depth of the hole, and thus can be promptly applied to the various holes. Furthermore, since the inserting part 280 at the base end side of the holding part 271 and the receiving part 282 at the tip of the head main body 220 are provided with tapered parts 280*a*, 282*a*, the holding part 271 can be easily centered with the head main body 220.

In the above, the preferred embodiments of the present invention are described, however: the present invention is not limited to the above embodiments, and may be embodied in various forms. For example, the holder and the head main body are jointed by providing the threaded part with respect to on another, however: the joint is not limited to them, and may be in any form as long as it is removable and installable. Moreover, the method of installing a mirror may not be a form in which slits are provided to the side surfaces of the inner tubular body, but be a form, for example, in which a holding member is disposed separately. Furthermore, the optical path changing device is not limited to a mirror, but may be a prism or the like.

The invention claimed is:

1. An inspection head supporting structure applied to a surface inspecting apparatus, which irradiates an inspection light to an inspection object from an outer circumference of an inspection head with rotating the inspection head around its axis, receives reflection light reflected from the inspection object to the inspection head, and inspects the surface of the inspection object on the basis of the light amount of the reflection light, wherein the inspection head comprises a hollow tubular bearing fitting part and a main shaft part extending to its tip side from the bearing fitting part, the inspection head supporting structure comprising:
a head supporting shaft disposed coaxially inside the bearing fitting part of the inspection head;
a pair of bearings, which are disposed with a distance from each other in an axial direction of the inspection head and between an outer circumference of the head supporting shaft and an inner circumference of the bearing fitting part, and which are capable of respectively applying a radial load and a unidirectional axial load;
inner race constraining devices, each of which constrains each inner race of the pair of bearings at a constant position in an axial direction on atop of the head supporting shaft;
a first and a second pressure preloading members in cylindrical or annular shapes, which are disposed juxtaposed between outer races of the pair of bearings in a movable manner in the axial direction relative to the inspection head;
a spring device which is disposed between the first and the second pressure preloading members and each of which urges each pressure preloading member toward each outer race of the pair of bearings;
a ring of elastic material disposed between the first pressure preloading member and an outer race of one of the bearings, and an outer circumference of the ring being contacted with the inner circumference of the bearing fitting part; and
outer race constraining devices each of which constrains each outer race of the pair of bearings from outside in the axial direction with a first constraining part, which is disposed within the bearing fitting part, and a second constraining part, which is disposed removably and installably at a base end part of the inspection head,
wherein, the inspection head is configured to be capable of taken out from atop of the pair of bearings toward the tip side in the axial direction, in a condition wherein the inspection head contains the bearing fitting part and the main shaft part, by removing the second constraining part from the inspection head.

2. The inspection head supporting structure according to claim 1, wherein, as the spring device, a plurality of spring members are disposed at equal spacing in a circumferential direction of the inspection head and between the first and the second pressure preloading members.

3. The inspection head supporting structure according to claim 1, wherein an O-ring is disposed as the ring of elastic material.

4. The inspection head supporting structure according to claim 1, wherein a fit tolerance between the outer race of the bearing and the bearing fitting part of the inspection head is set in a loose fit region.

5. The inspection head supporting structure according to claim 1, wherein the bearing fitting part of the inspection head is formed in a monolithic structure in which the bearing fitting part is unable to be dismantled from the main shaft part.

6. A surface inspecting apparatus which moves a shaft-like inspection head along its axis with rotating the inspection head around the axis by a drive device, wherein an optical path changing device is provided to a tip of the shaft-like inspection head, and which concurrently changes an optical path of an inspection light incident along the axis into an interior of the inspection head with the optical path changing device, irradiates the inspection light whose optical path is changed to an inspection object, and detects surface condition of the inspection object on the basis of the light amount of the inspection light reflected by the inspection object and incident again into the interior of the inspection head, wherein
the inspection head comprises a head main body attached to a drive device, and a holding part which is provided removably and installably to the head main body and which holds the optical path changing device, and
the holding part comprises an outer tubular body, which is removable from and installable to the head main body, and an inner tubular body, which holds the optical path changing device and is removable from and installable into an interior of the outer tubular body.

7. The surface inspecting apparatus according to claim 6, wherein the holding part is disposed in a limited manner at the tip side of the inspection head.

8. The surface inspecting apparatus according to claim 6, wherein
the inspection head comprises an inserting part to be inserted into the inspection object, and
the holding part extends toward a side of the drive mechanism farther than the inserting part does.

9. The surface inspecting apparatus according to claim 6, wherein
a tip of the outer tubular body is closed, and a translucent hole is provided to a tubular side surface of the outer tubular body,
the both ends of the inner tubular body are opened, a translucent hole is provided to a tubular side surface of the inner tubular body, and a translucent member is fitted into the translucent hole, and
slits are provided to the inner surface of the tubular side surface so as to be symmetrical with respect to the translucent hole and be inclined at a prescribed angle relative to an axis of the inner tubular body.

10. The surface inspecting apparatus according to claim 7, wherein
a tip of the outer tubular body is closed, and a translucent hole is provided to a tubular side surface of the outer tubular body,
the both ends of the inner tubular body are opened, a translucent hole is provided to a tubular side surface of the inner tubular body, and a translucent member is fitted into the translucent hole, and
slits are provided to the inner surface of the tubular side surface so as to be symmetrical with respect to the translucent hole and be inclined at a prescribed angle relative to an axis of the inner tubular body.

11. The surface inspecting apparatus according to claim 8, wherein
a tip of the outer tubular body is closed, and a translucent hole is provided to a tubular side surface of the outer tubular body,
the both ends of the inner tubular body are opened, a translucent hole is provided to a tubular side surface of the inner tubular body, and a translucent member is fitted into the translucent hole, and
slits are provided to the inner surface of the tubular side surface so as to be symmetrical with respect to the translucent hole and be inclined at a prescribed angle relative to an axis of the inner tubular body.

* * * * *